(12) United States Patent
Ailinger et al.

(10) Patent No.: US 9,538,904 B2
(45) Date of Patent: Jan. 10, 2017

(54) SPIRAL UNIT, INSERTION APPARATUS, AND MANUFACTURING METHOD OF SPIRAL UNIT

(71) Applicant: OLYMPUS CORPORATION, Tokyo (JP)

(72) Inventors: Robert E. Ailinger, Norwood, MA (US); James J. Frassica, Chelmsford, MA (US); Richard M. Andrews, Lincoln, RI (US); Hiroaki Miyoshi, Fuchu (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 14/974,752

(22) Filed: Dec. 18, 2015

(65) Prior Publication Data
US 2016/0100743 A1 Apr. 14, 2016

Related U.S. Application Data

(63) Continuation of application No. PCT/JP2014/065376, filed on Jun. 10, 2014.
(Continued)

(51) Int. Cl.
*A61B 1/00* (2006.01)
*G02B 23/24* (2006.01)
(Continued)

(52) U.S. Cl.
CPC .......... *A61B 1/0011* (2013.01); *A61B 1/0016* (2013.01); *A61B 1/00154* (2013.01);
(Continued)

(58) Field of Classification Search
CPC . A61B 1/0011; A61B 1/0016; A61B 1/00154; B29C 65/1403; G02B 23/2476; A61M 25/01; B29L 2031/7546
See application file for complete search history.

(56) References Cited

U.S. PATENT DOCUMENTS

| 5,416,303 A * | 5/1995 | Grooms ................. B29C 65/18 156/274.2 |
| 2012/0002981 A1 | 1/2012 | Park |
| 2012/0316393 A1 * | 12/2012 | Frassica .......... A61B 17/12099 600/118 |

FOREIGN PATENT DOCUMENTS

| JP | H06-315978 A | 11/1994 |
| JP | H07-117132 A | 5/1995 |

(Continued)

OTHER PUBLICATIONS

English translation of International Preliminary Report on Patentability dated Jan. 7, 2016 together with the Written opinion received in related International Application No. PCT/JP2014/065376.
(Continued)

*Primary Examiner* — Timothy J Neal
(74) *Attorney, Agent, or Firm* — Scully, Scott, Murphy & Presser, P.C.

(57) ABSTRACT

A spiral unit includes a base tube extended along a longitudinal axis and made of a first thermoplastic resin, and a fin disposed on an outer peripheral surface of the base tube along a fin axis spirally extended around the longitudinal axis and made of a second thermoplastic resin. The fin includes a strip portion provided in a state of being bonded to the outer peripheral surface of the base tube and spirally extended along the fin axis. The second resin being mixed with a magnetic material in the strip portion.

6 Claims, 9 Drawing Sheets

Related U.S. Application Data

(60) Provisional application No. 61/839,431, filed on Jun. 26, 2013.

(51) Int. Cl.
    *A61M 25/01*     (2006.01)
    *B29C 65/14*     (2006.01)
    *A61B 1/04*     (2006.01)
    *A61B 17/00*     (2006.01)
    *B29K 101/12*     (2006.01)
    *B29L 31/00*     (2006.01)

(52) U.S. Cl.
    CPC ......... *A61M 25/01* (2013.01); *B29C 65/1403* (2013.01); *G02B 23/2476* (2013.01); *A61B 2017/00876* (2013.01); *B29K 2101/12* (2013.01); *B29L 2031/7546* (2013.01)

(56) References Cited

FOREIGN PATENT DOCUMENTS

| | | |
|---|---|---|
| JP | 2004-232674 A | 8/2004 |
| JP | 2007-314711 A | 12/2007 |
| JP | 2013-525076 A | 6/2013 |
| WO | WO 2012/137363 A1 | 10/2012 |

OTHER PUBLICATIONS

International Search Report dated Jul. 8, 2014 issued in PCT/JP2014/065376.

Japanese Office Action dated Jun. 23, 2015 issued in JP 2015-522307.

\* cited by examiner

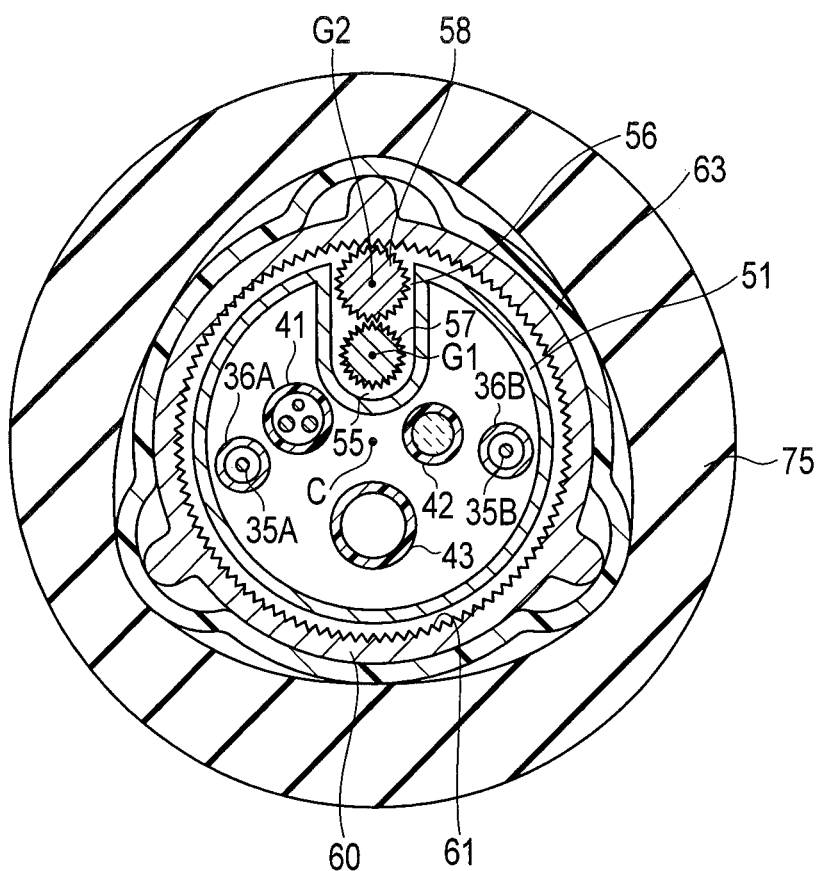
F I G. 3

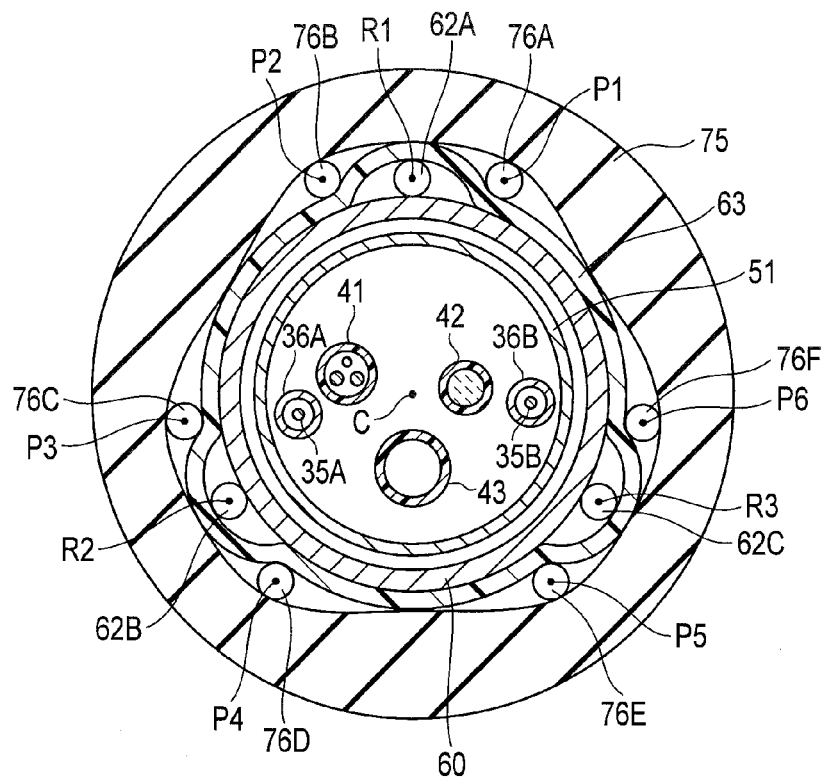
F I G. 4
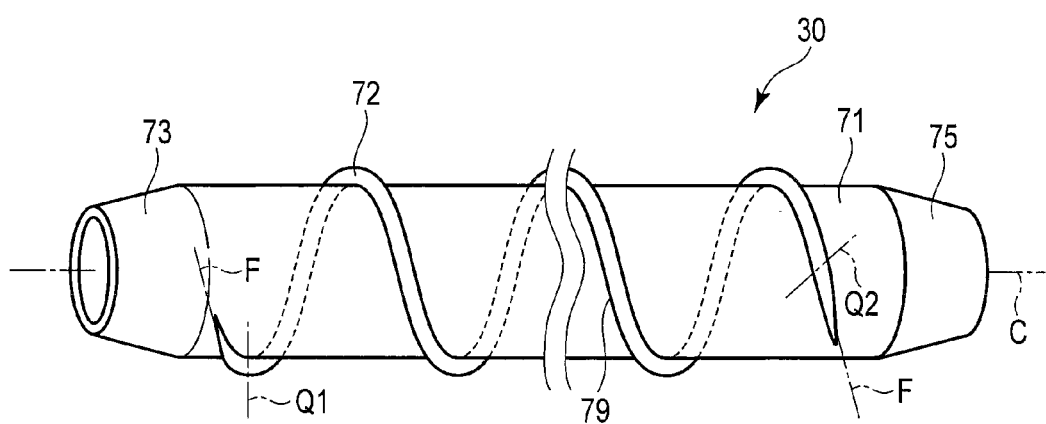
F I G. 5

SPIRAL UNIT, INSERTION APPARATUS, AND MANUFACTURING METHOD OF SPIRAL UNIT

CROSS-REFERENCE TO RELATED APPLICATIONS

This is a Continuation Application of PCT Application No. PCT/JP2014/065376, filed Jun. 10, 2014 and based upon and claiming the benefit of priority from prior U.S. Provisional Application No. 61/839,431, filed Jun. 26, 2013, the entire contents of which are incorporated herein by reference.

BACKGROUND OF THE INVENTION

1. Field of the Invention

The present invention relates to a spiral unit having a fin spirally disposed around a longitudinal axis on an outer peripheral surface of a base tube extended along the longitudinal axis. Further, it also relates to an insertion apparatus provided with this spiral unit, and a manufacturing method of this spiral unit.

2. Description of the Related Art

Specification of U.S. Patent Application Publication No. 2012/002981 discloses a spiral unit which is attached to an inserting section of an insertion apparatus, e.g., an endoscope apparatus. This spiral unit includes a base tube extended along a longitudinal axis, and a fin disposed on an outer peripheral surface of the base tube along a fin axis spirally extended around the longitudinal axis. The base tube and the fin are made of a rein. In a state where the spiral unit is attached to the inserting section, the base tube and the fin can rotate together in a periaxial direction of the longitudinal axis with respect to the inserting section. When the base tube and the fin rotate in a state where the fin abuts on a paries portion of a lumen paries or the like, propulsive force in a distal direction or a proximal direction acts on the inserting section.

BRIEF SUMMARY OF THE INVENTION

According to one aspect of the invention, a spiral unit includes: a base tube which is extended along a longitudinal axis, and which is made of a first thermoplastic resin; a fin which is disposed on an outer peripheral surface of the base tube along a fin axis spirally extended around the longitudinal axis, and which is made of a second thermoplastic resin, the fin including a hollow portion in which a cavity portion is formed along the fin axis; a strip portion which is provided in a state of being bonded to the outer peripheral surface of the base tube in the fin, and which is spirally extended along the fin axis on an inner peripheral direction side of the cavity portion; and a magnetic material which is mixed with the second resin in the strip portion, and which is configured to generate heat when vibrated to fuse the second resin.

According to one another aspect of the invention, a manufacturing method of a spiral unit, including: forming a base tube along a longitudinal axis from a first thermoplastic resin; forming a fin along a fin axis from a second thermoplastic resin, the fin being formed in a state where a strip portion in which the second resin is mixed with a magnetic material is extended along the fin axis; winding the fin on an outer peripheral surface of the base tube in a state where the fin axis is spirally extended around the longitudinal axis, the fin being wound in a state where the strip portion abuts on the outer peripheral surface of the base tube; and generating heat in the strip portion by applying electromagnetic waves to vibrate the magnetic material, the heat performing at least one of fusing the second resin in the strip portion and fusing the first resin in an abutting portion of the base tube to the strip portion, and thereby bonding the strip portion to the outer peripheral surface of the base tube.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 3 is a cross-sectional view taken along a line III-III in FIG. 2;

FIG. 4 is a cross-sectional view taken along a line IV-IV in FIG. 2;

FIG. 5 is a perspective view schematically showing a configuration of a spiral unit according to the first embodiment;

DETAILED DESCRIPTION OF THE INVENTION

First Embodiment

A first embodiment according to the present invention will now be described with reference to FIG. 1 to FIG. 10. FIG.

Figure 1:
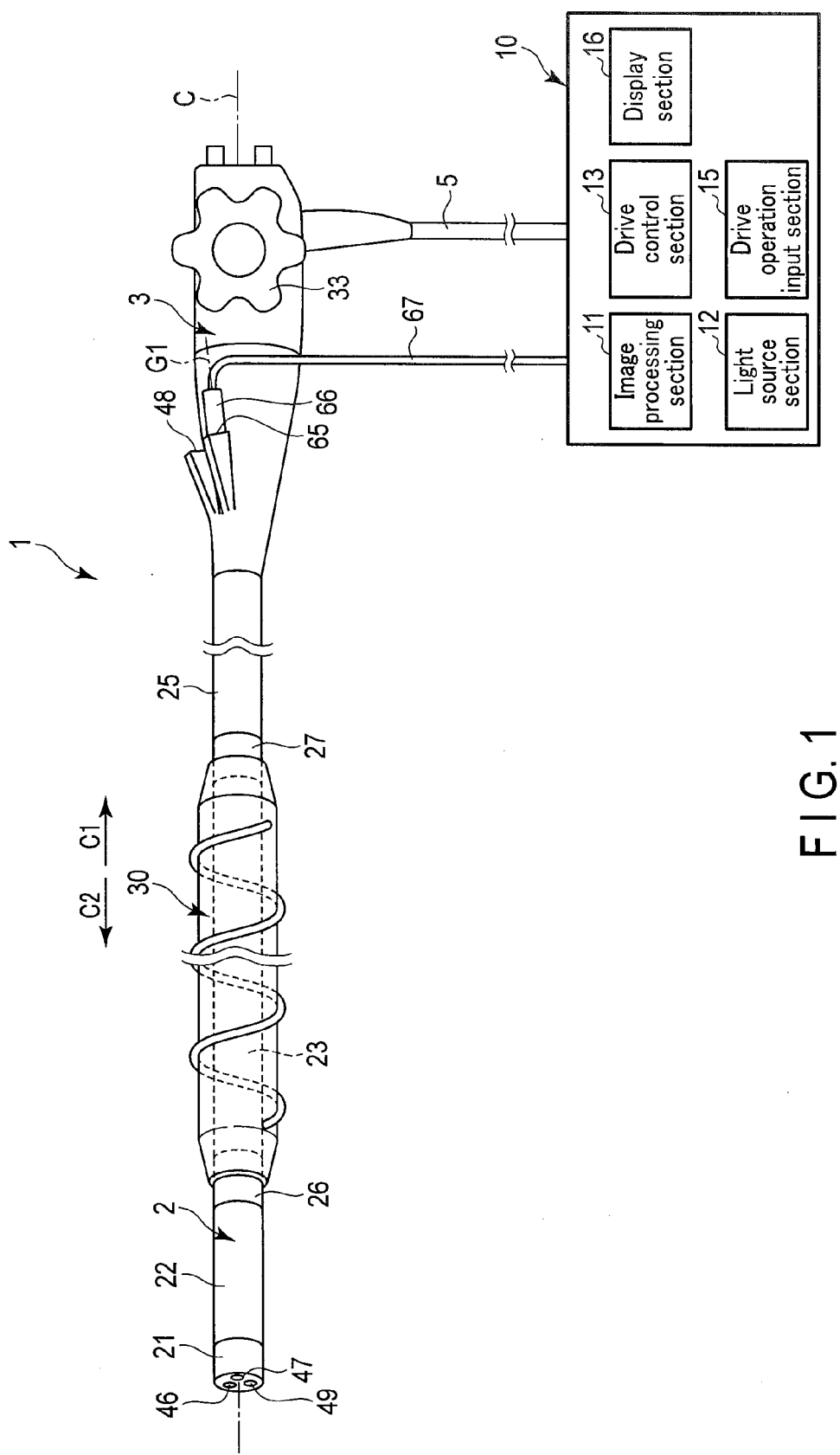
FIG. 1 is a schematic view showing an endoscope apparatus according to a first embodiment.

1 is a view showing an endoscope apparatus 1 which is an insertion apparatus according to the first embodiment. As shown in FIG. 1, the endoscopic device 1 has a longitudinal axis C. One side (a direction of an arrow C1 in FIG. 1) of direction parallel to the longitudinal axis C is a distal direction, and an opposite side (a direction of an arrow C2 in FIG. 1) to the distal direction is a proximal direction. Further, it is assumed that a direction to get away from the longitudinal axis C in a cross section perpendicular to the longitudinal axis C is an outer peripheral direction, and a direction to get close to the longitudinal axis C in the cross section perpendicular to the longitudinal axis C is an inner peripheral direction. Further, the outer peripheral direction and the inner peripheral direction correspond to a radial direction. The endoscope apparatus 1 includes an inserting section (an endoscope inserting section) 2 extended along the longitudinal axis C, and an operating section (an endoscope operating section) 3 provided on a proximal direction side with respect to the inserting section 2. The inserting section 2 is extended along the longitudinal axis C, and inserted into a body cavity (a lumen) when the endoscope apparatus 1 is used.

One end of a universal cable 5 is connected to the operating section 3. The other end of the universal cable 5 is connected to a peripheral unit 10. The peripheral unit 10 includes an image processing section 11 such as an image processor, a light source section 12, a drive control section 13 which is a control device including a central processing unit (CPU), an application specific integrated circuit (ASI), or the like, a drive operation input section 15 such as a footswitch, a button, or the like, and a display section 16 such as a monitor.

The inserting section 2 includes a distal rigid section 21 which forms a distal end of the inserting section, a bending section 22 provided on the proximal direction side with respect to the distal rigid section 21, a first flexible tube section 23 provided on the proximal direction side with respect to the bending section 22, and a second flexible tube section 25 provided on the proximal direction side with respect to the first flexible tube section 23. The bending section 22 is connected to the first flexible tube section 23 via a first relay connecting section 26. Furthermore, the first flexible tube section 23 is connected to the second flexible tube section 25 via a second relay connecting section 27.

A spiral unit 30 is provided on an outer peripheral direction side of the inserting section 2. The spiral unit 30 is extended along the longitudinal axis C between the first relay connecting section 26 and the second relay connecting section 27. In a state where the inserting section 2 is inserted through the spiral unit 30, the spiral unit 30 is attached to the inserting section. In this embodiment, the spiral unit 30 can rotate in a periaxial direction of the longitudinal axis relative to the inserting section.

Figure 2:
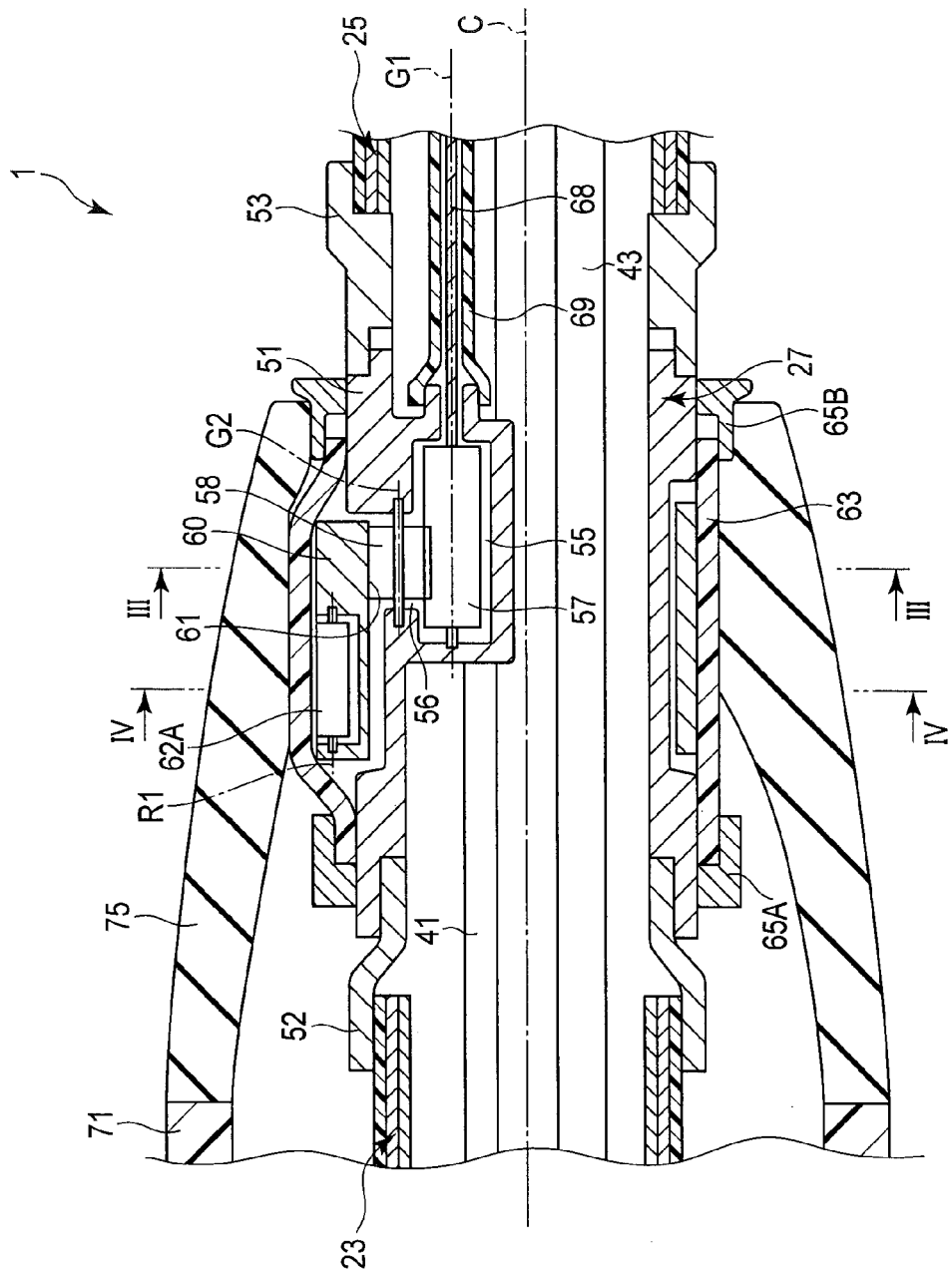
FIG. 2 is a cross-sectional view schematically showing a configuration of a second relay connecting section of an inserting section of the endoscope apparatus according to the first embodiment.

FIG. 2 is a view showing a configuration of the second relay connecting section 27. Moreover, FIG. 3 is cross-sectional view taken along a line in FIG. 2, and FIG. 4 is a cross-sectional view taken along a line IV-IV in FIG. 2. As shown in FIG. 1, a bending operation knob 33 that is a bending operation input section in which a bending operation of the bending section 2 is input is provided on an outer surface of the operating section 3. As shown in FIG. 3 and FIG. 4, in the inserting section 2, bending wires 35A and 35B are extended along the longitudinal axis C. In the operating section 3, proximal ends of the bending wires 35A and 35B are connected to a pulley (not shown) coupled with the bending operation knob 33. Distal ends of the bending wires 35A and 35B are connected to a distal portion of the bending section 22. A bending operation of the bending operation knob 33 enables pulling of the bending wire 35A or the bending wire 35B, whereby the bending section 22 bends.

Each of the bending wires 35A and 35B are inserted through a corresponding coil 36A or 36B. Proximal ends of the coils 36A and 36B are fixed to an inner peripheral surface of the operating section 3. Additionally, distal ends of the coils 36A and 36B are connected to an inner peripheral surface of the first relay connecting section 26. It is to be noted that, in this embodiment, the two bending wires 35A and 35B are provided so that the bending section 22 can bend in two directions but, for example, four bending wires may be provided so that the bending section 22 can bend in four directions.

As shown in FIG. 2 to FIG. 4, in the inserting section 2, an imaging cable 41, a light guide 42, and a treatment tool channel tube 43 are extended along the longitudinal axis C. In the distal rigid section 21 (a distal portion of the inserting section 2), an imaging element (not shown) which acquires an image of a subject is provided. The imaging element acquires an image of the subject through an observation window 46. A distal end of the imaging cable 41 is connected to the imaging element. The imaging cable 41 is extended through the inside of the inserting section 2, the inside of the operating section 3, and the inside of the universal cable 5, and a proximal end of the imaging cable 41 is connected to the image processing section 11 in the peripheral unit 10. An acquired subject image is subjected to image processing by the image processing section 11, whereby an image of the subject is generated. Further, the generated image of the subject is displayed in the display section 16.

Furthermore, the light guide 42 is extended through the inside of the inserting section 2, the inside of the operating section 3, and the inside of the universal cable 5, and a proximal end of the light guide 42 is connected to the light source section 12 in the peripheral unit 10. Light exiting from the light source section 12 is guided by the light guide 42, and applied to the subject from an illumination window 47 of the distal portion (the distal rigid section 21) of the inserting section 2.

As shown in FIG. 1, on the outer surface of the operating section 3, a treatment tool inserting section 48 into which a treatment tool such as a forceps is inserted is provided. A proximal end of the treatment tool channel tube 43 is connected to the treatment tool inserting section 48 through the inside of the inserting section 2 and the inside of the operating section 3. The treatment tool inserted from the treatment tool inserting section 48 protrudes from an opening portion 49 of the distal rigid section 21 toward the distal direction through the inside of the treatment tool channel tube 43. Furthermore, in a state where the treatment tool protrudes from the opening portion 49 of the distal rigid section 21, a treatment is conducted by using the treatment tool.

As shown in FIG. 2, in the second relay connecting section 27, a base member 51 is provided. A proximal portion of the first flexible tube section 23 is coupled with a distal portion of the base member 51 via a relay member 52. Consequently, the first flexible tube section 23 is coupled with the second relay connecting section 27. Moreover, a distal portion of the second flexible tube section 25 is coupled with a proximal portion of the base member 51 via a relay member 53. Consequently, the second flexible tube section 25 is coupled with the second relay connecting section 27.

As shown in FIG. 2 to FIG. 4, in the second relay connecting section 27, a cavity portion 55 is formed by the base member 51. The cavity portion 55 is opened toward the outer peripheral direction at an opening portion 56. Additionally, a drive gear 57 and a relay gear 58 are attached to the base member 51. The drive gear 57 is arranged in the cavity portion 55, and the relay gear 58 is arranged near the opening portion 56 of the cavity portion 55. The drive gear 57 is meshed with a relay gear 58. The drive gear 57 can rotate around a drive axis G1, and the relay gear 58 can rotate around a gear axis G2.

A rotary tubular member 60 is attached to the base member 51 of the second relay connecting section 27. In a state where the inserting section 2 is inserted through the rotary tubular member 60, the rotary tubular member 60 is connected to the base member 51. The rotary tubular member 60 can rotate in the periaxial direction of the longitudinal axis with respect to the inserting section 2 (the base member 51). On an inner peripheral surface of the rotary tubular member 60, an inner peripheral gear 61 is provided over the entire circumference in the periaxial direction of the longitudinal axis. The inner peripheral gear section 61 is meshed with the relay gear 58.

In this embodiment, three inner rollers 62A to 62C are attached to the rotary tubular member 60. The inner rollers 62A to 62C are arranged at substantially equal intervals in the periaxial direction of the longitudinal axis. Each of the inner rollers 62A to 62C has a corresponding roller axis (one of R1 to R3). Each of the inner rollers 62A to 62C can rotate around the corresponding roller axis (one of R1 to R3) relative to the rotary tubular member 60. Further, the inner rollers 62A to 62 can rotate together with the rotary tubular member 60 to the inserting section 2 (the base member 51) in the periaxial direction of the longitudinal axis.

The outer peripheral direction side of the rotary tubular member 60 and the inner rollers 62A to 62C is covered with a tubular cover member 63. A distal end of the cover member 63 is fixed to the base member 51 by a locking member 65A, and a proximal end of the cover member 63 is fixed to the base member 51 by a locking member 65B. At a fixing position of the distal end of the cover member 63 and a fixing position of the proximal end of the cover member 63, liquid-tightness is maintained between the base member 51 and the cover member 63. Consequently, a liquid is prevented from flowing into the cavity portion 55, the rotary tubular member 60, and the inner rollers 62A to 62C which are placed on the inner peripheral direction side with respect to the cover member 63. Furthermore, in regions where the inner rollers 62A to 62C are placed in the periaxial direction of the longitudinal axis, the cover member 63 protrudes toward the outer peripheral direction. It is to be noted that the cover member 63 is fixed to the inserting section 2, and the rotary tubular member 60 can rotate in the periaxial direction of the longitudinal axis relative to the cover member 63.

As shown in FIG. 1, on the outer surface of the operating section 3, a member inserting section 65 is provided. Moreover, a motor 66 which is a drive member is attached to the member inserting section 65. One end of a motor cable 67 is connected to the motor 66. The other end of the motor cable 67 is connected to the drive control section 13 in the peripheral unit 10.

As shown in FIG. 2, inside the second flexible tube section 25 of the inserting section 2, a drive shaft 68 which is a line member is extended along the drive axis G1 is extended. A distal end of the drive shaft 68 is connected to the drive gear 57. A proximal end of the drive shaft 68 is connected to the motor 66 attached to the member inserting section 65. Additionally, a distal end of a member channel tube 69 is connected to the base member 51. A proximal end of the member channel tube 69 is connected to the member inserting section 65. The drive shaft 68 is extended through the inside of the member channel tube 69.

Based on input of an operation in the drive operation input section 15, the drive control section 13 supplies electric power to the motor 66 through the motor cable 67, and performs drive control over the motor 66. When the motor 66 is driven, rotational drive force to rotate the spiral unit 30 is generated, and the drive shaft 68 and the drive gear 57 rotate around the drive axis G1. Here, the drive axis G1 runs through the center of the drive gear 57 and the drive shaft 68, and is substantially parallel to the longitudinal axis C in the second flexible tube section 25. Further, the drive axis G1 bends toward the member inserting section 65 in the operating section 3.

When the drive gear 57 rotates, the relay gear 58 rotates around the gear axis G2, and the rotational drive force is transmitted to the rotary tubular member 60 through the relay gear 58. Consequently, the rotary tubular member 60 rotates in the periaxial direction of the longitudinal axis, and the inner rollers 62A to 62C move in the periaxial direction of the longitudinal axis relative to the inserting section 2 and the cover member 63.

FIG. 5 is a view showing a configuration of the spiral unit 30. As shown in FIG. 5, the spiral unit 30 includes a base tube 71 extended along the longitudinal axis C. The base tube 71 is made of a first thermoplastic resin. Furthermore, a fin 72 is disposed on an outer peripheral surface of the base tube 71. The fin is made of a second thermoplastic resin such as polyvinyl chloride (PVC). Moreover, the fin 72 has a fin axis F spirally extended around the longitudinal axis C, and the fin 72 is provided along the fin axis F. It is to be noted that the first resin forming the base tube 71 and the second resin forming the fin 72 may be the same rein or may be different resins.

On a distal direction side of the base tube 71, a tubular distal side taper portion 73 is provided. The distal side taper portion 73 is formed into a taper shape whose outer diameter decreases toward the distal direction side. Moreover, on a proximal direction side of the base tube 71, a tubular proximal side taper portion 75 is provided. The proximal side taper portion 75 is formed into a taper shape whose outer diameter decreases toward the proximal direction side. It is to be noted that, in FIG. 5, the fin 72 is extended only on the outer peripheral surface of the base tube 71, and it is not extended on an outer peripheral surface of the distal side taper portion 73 and an outer peripheral surface of the proximal side taper portion 75, but the fin 72 may be extended on the outer peripheral surface of the distal side taper portion 73 and the outer peripheral surface of the proximal side taper portion 75.

As shown in FIG. 4, six outer rollers 76A to 76F are disposed on an inner peripheral surface of the proximal side taper portion 75. The outer rollers 76A to 76F are placed on the outer peripheral direction side with respect to the cover member 63. In the periaxial direction of the longitudinal axis, the inner roller 62A is placed between the outer roller 76A and the outer roller 76B, and the inner roller 62B is placed between the outer roller 76C and the outer roller 76D. Additionally, in the periaxial direction of the longitudinal axis, the inner roller 62C is placed between the outer roller 76E and the outer roller 76F. Each of the outer rollers 76A to 76F has a corresponding roller axis (one of P1 to P6). Each of the outer rollers 76A to 76F can rotate around the corresponding roller axis (one of P1 to P6) relative to the cover member 63 and the proximal side taper portion 75. Further, the outer rollers 76A to 76F can rotate together with the spiral unit 30 in the periaxial direction of the longitudinal axis relative to the inserting section 2 (the base member 51).

When the rotary tubular member 60 rotates by driving of the motor 66 as described above, the inner roller 62A pushes the outer roller 76A or the outer roller 76B. Likewise, the inner roller 62C pushes the outer roller 76C or the outer roller 76D, and the inner roller 62C pushes the outer roller 76E or the outer roller 76F. Consequently, the rotational drive force is transmitted from the inner rollers 62A to 62C to the spiral unit 30, and the spiral unit 30 including the base tube 71 and the fin 72 rotate in one side of the periaxial direction of the longitudinal axis relative to the inserting section 2 and the cover member 63.

It is to be noted that, since each of the inner rollers 62A to 62C rotates around the corresponding roller axis (one of R1 to R3), friction between the respective inner rollers 62A to 62C and the cover member 63 is reduced. Likewise, since each of the outer rollers 76A to 76F rotates around the corresponding roller axis (one of P1 to P6), friction between the respective outer rollers 76A to 76F and the cover member 63 is reduced. Thus, the rotational drive force is appropriately transmitted from the inner rollers 62A to 62C to the spiral unit 30, and the spiral unit 30 appropriately rotates. In a state where the fin 72 abuts on a paries portion of a lumen paires or the like, the spiral unit 30 (the base tube 71 and the fin 72) rotates, and hence propulsive force toward the distal direction or the proximal direction acts on the inserting section 2.

Figure 6:
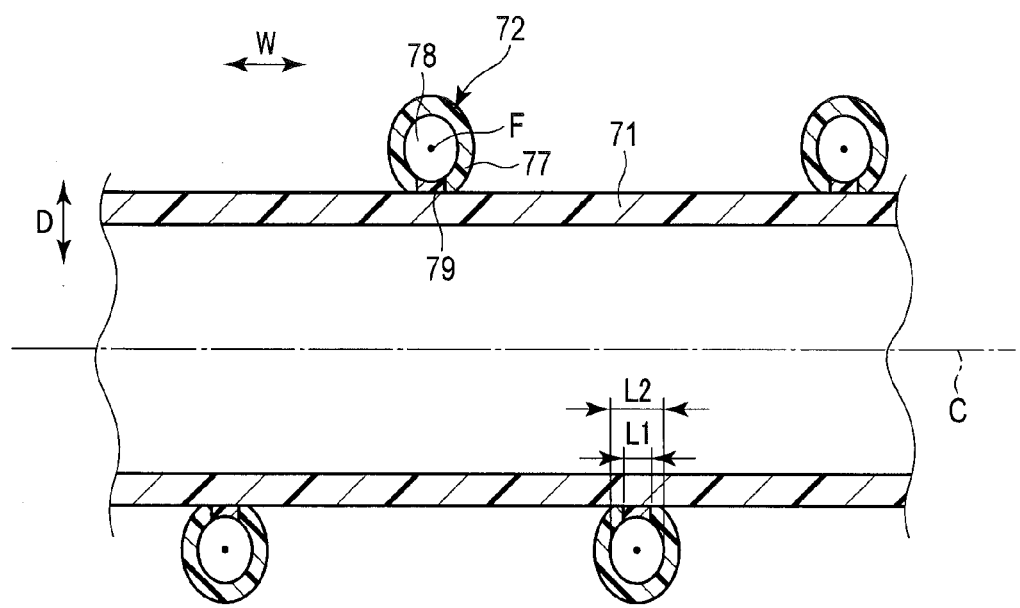
FIG. 6 is a cross-sectional view schematically showing a base tube and a fin in a cross section parallel to a longitudinal axis in the spiral unit according to the first embodiment.

FIG. 6 is a view of a spiral unit 30 taken along a cross section parallel to the longitudinal axis C. In FIG. 6, the fin 72 is taken along a cross section perpendicular to the fin axis F. As shown in FIG. 6, the fin 72 includes a hollow portion 77, and is formed into a tubular shape extended along the fin axis F. Thus, in the hollow portion 77, a cavity portion 78 is extended along the fin axis F. Here, since the fin axis F is spirally extended around the longitudinal axis C, the cavity portion 78 is also spirally extended around the longitudinal axis C. It is to be noted that, in this embodiment, the fin axis F coincides with a central axis of the cavity portion 78.

Further, in the fin 72, a strip portion 79 is provided on an inner peripheral direction side with respect to the cavity portion 78. The strip portion 79 is extended along the fin axis F. That is, the band portion 79 is spirally extended around the longitudinal axis C. The fin is bonded to the outer peripheral surface of the base tube 71 at the strip portion 79. In the belt portion 79, the second resin forming the fin 72 is mixed with a magnetic material such as iron, ferrite, stainless, or ceramics.

Here, a direction to get close to the longitudinal axis C is the inner peripheral direction, and a direction to get away from the longitudinal axis C is the outer peripheral direction. Furthermore, the outer peripheral direction and the inner peripheral direction are a radial direction of the base tube 71 (a direction of an arrow D in FIG. 6). Moreover, a direction that is perpendicular to the fin axis F and perpendicular to the radial direction of the base tube 71 is a fin width direction (a direction of an arrow W in FIG. 6). A strip width dimension L1 of the strip portion 79 in the fin width direction is smaller than a cavity width dimension L2 of the cavity portion 78 in the fin width direction.

As shown in FIG. 5, a protrusion amount of the fin 72 toward the outer periphery from the outer peripheral surface of the base tube 71 is constant between a distal side reference position Q1 and a proximal side reference position Q2. On the distal direction side with respect to the distal side reference position Q1, the protrusion amount of the fin 72 from the outer peripheral surface of the base tube 71 is reduced as getting toward the distal direction. Further, on the proximal direction side with respect to the proximal side reference position Q2, the protrusion amount of the fin 72 from the outer peripheral surface of the base tube 71 is reduced as getting toward the proximal direction. Thus, the protrusion amount of the fin 72 from the outer peripheral surface of the base tube 71 becomes maximum between the distal side reference position Q1 and the proximal side reference position Q2. Furthermore, the strip portion 79 is extended along the fin axis F between the distal side reference position Q1 and the proximal side reference position Q2.

Figure 7:
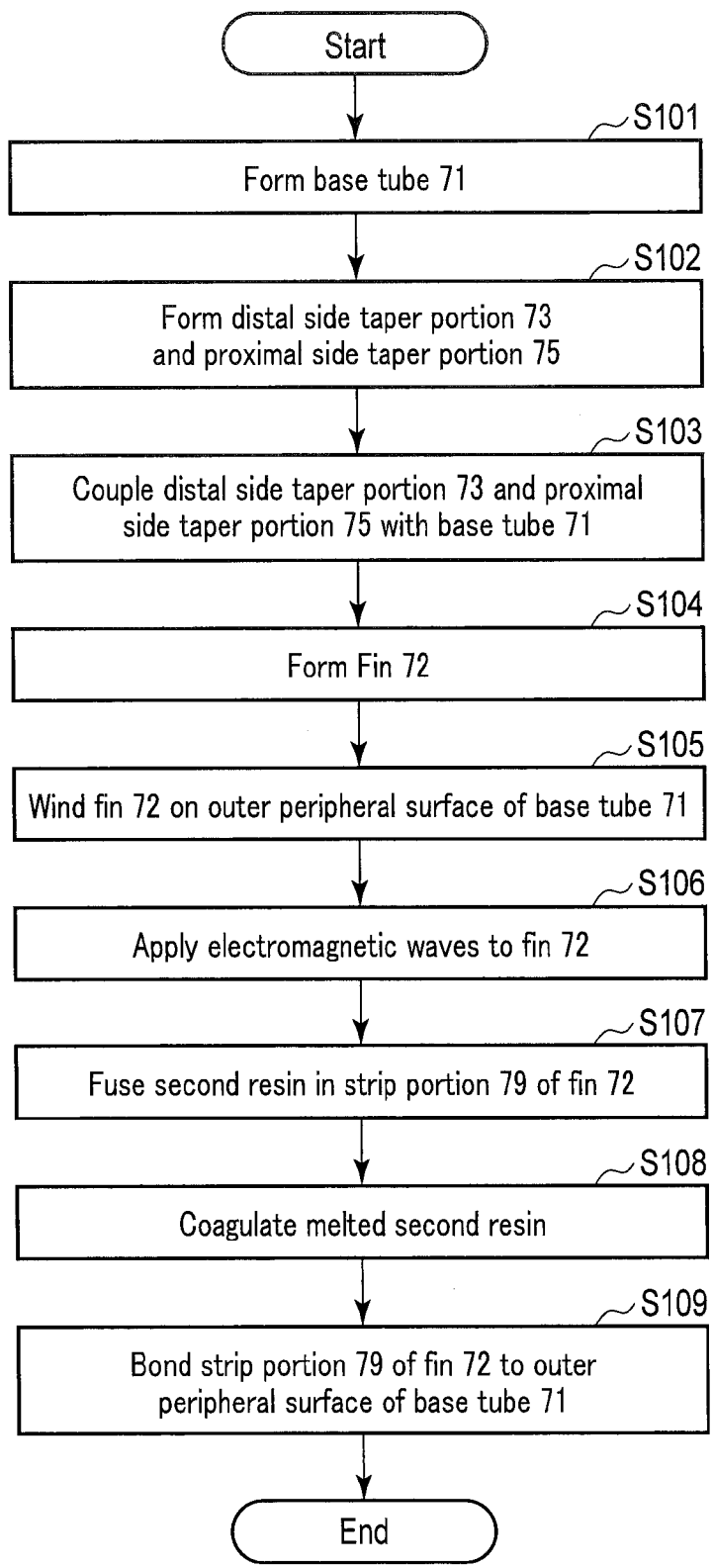
FIG. 7 is a flowchart showing a manufacturing method of a spiral unit according to the first embodiment.

A manufacturing method of the spiral unit 30 will now be described. FIG. 7 is a flowchart showing the manufacturing method of the spiral unit 30. As shown in FIG. 7, in manufacture of the spiral unit 30, the base tube 71 is first formed along the longitudinal axis C from the first thermoplastic resin (a step S101). The base tube 71 is formed by extrusion molding. Moreover, the distal side taper portion 73 and the proximal side taper portion 75 are formed (a step S102), and the distal side taper portion 73 and the proximal side taper portion 75 are coupled with the base tube 71 (a step S103). It is to be noted that, in this embodiment, the distal side taper portion 73 and the proximal side taper portion 75 are members different from the base tube 71, but they may be integrally formed with the base tube 71.

Figure 8:
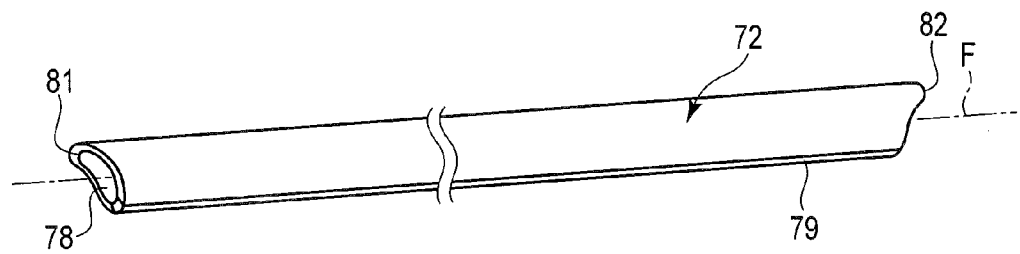
FIG. 8 is a perspective view schematically showing an example of the fin according to the first embodiment in a state before being wound on an outer peripheral surface of the base tube.
Figure 9:
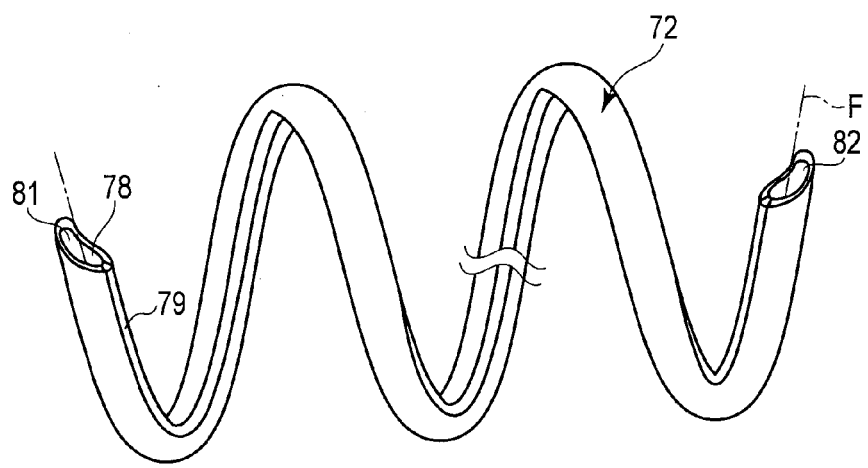
FIG. 9 is a perspective view schematically showing another example of the fin according to the first embodiment in a state before being wound on an outer peripheral surface of the base tube different from FIG. 8.

Additionally, the fin 72 is formed along the fin axis F from the second thermoplastic resin (a step S104). The fin 72 is formed by two-color extrusion molding. When the two-color extrusion molding is performed, the strip portion 79 containing the magnetic material and other portions containing no magnetic material except for the strip portion 79 can be readily formed. In the extrusion-molded fin 72, the band portion 79 is extended along the fin axis F. FIG. 8 shows an example of the fin 72 in a state before being wound on the outer peripheral surface of the base tube 71. In the distal portion of the fin 72, a distal side inclined surface 81 that is inclined relative to the fin axis F is provided in a state of being extended from the distal end of the belt portion 79 toward the distal direction along the fin axis F. Further, in a proximal portion of the fin 72, a proximal side inclined surface 82 that is inclined relative to the fin axis F is provided in a state of being extended from the proximal end of the strip portion 79 toward the proximal direction along the fin axis F. Each of the distal side inclined surface 81 and the proximal side inclined surface 82 is formed into a face shape corresponding to a curved shape of the outer peripheral surface of the base tube 71. Furthermore, FIG. 9 shows another example of the fin 72 in a state before being wound on the outer peripheral surface of the base tube 71. In the distal portion of the fin 72, the distal side inclined surface 81 that is inclined relative to the fin axis F is provided in a state of being extended from the distal end of the strip portion 79 toward the distal direction along the fin axis F. Moreover, in the proximal end portion of the fin 72, the proximal side inclined surface 82 that is inclined relative to the fin axis F is provided in a state of being extended from the proximal end of the strip portion 79 toward the proximal direction along the fin axis F. Each of the distal side inclined surface 81 and the proximal side inclined surface 82 is formed into a face shape corresponding to a curved shape of the outer peripheral surface of the base tube 71. As shown in FIG. 8, in the fin 72 in a state before being wound on the outer peripheral surface of the base tube 71, the fin axis F may be linearly extended. Additionally, as shown in FIG. 9, in the fin 72 in a state before being wound on the outer peripheral surface of the base tube 71, the fin axis F may be spirally extended.

Figure 10:
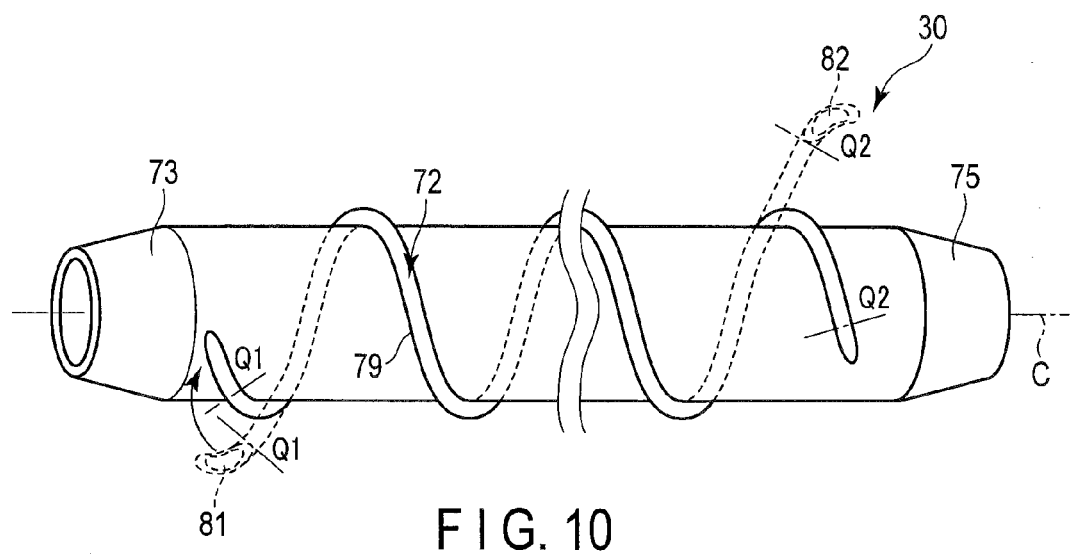
FIG. 10 is a perspective view schematically showing the fin according to the first embodiment in a state of being wound on the outer peripheral surface of the base tube.

Further, the fin 72 is wound on the outer peripheral surface of the base tube 71 in a state where the fin axis F is spirally extended around the longitudinal axis C (a step S105). FIG. 10 is a view showing a state where the fin 72 is wound on the outer peripheral surface of the base tube 71. As shown in FIG. 10, the fin 72 is wound in a state where the strip portion 79 abuts on the outer peripheral surface of the base tube 71. Furthermore, the distal side inclined surface 81 inclined relative to the fin axis F is formed in the distal portion of the fin 72, and the proximal side inclined surface 82 inclined relative to the fin axis F is formed in the proximal portion of the fin 72. The distal side inclined surface 81 and the proximal side inclined surface 82 are formed by cutting the fin 72 at cross sections inclined relative to the fin axis F.

The distal side inclined surface 81 abutting on the outer peripheral surface of the base tube 71 is inclined in a state of being placed toward the distal direction side as getting away from the strip portion 79. Moreover, a boundary between the distal side inclined surface 81 and the strip portion 79 is the distal side reference position Q1. Additionally, the proximal side inclined surface 82 abutting on the outer peripheral surface of the base tube 71 is inclined in a state of being placed toward the proximal direction side as getting away from the strip portion 79. Further, a boundary between the proximal side inclined surface 82 and the strip portion 79 is the proximal side reference position Q2. At this time, the strip portion 79 is extended from the distal side reference position Q1 to the proximal side reference position Q2, and the fin 72 abuts on the outer peripheral surface of the base tube 71 between the distal side reference position Q1 and the proximal side reference position Q2.

Furthermore, electromagnetic waves are applied to the fin 72 wound on the outer peripheral surface of the base tube 71 (a step S106). When the electromagnetic waves are applied, the magnetic material vibrates, and heat is generated in the strip portion 79. The second resin is fused in the strip portion 79 by the heat (a step S107). It is to be noted that the first resin may be fused in a portion of the base tube 71 abutting on the strip portion 79 by the generated heat. However, the second resin is not fused in other portions containing no magnetic material than the strip portion 79 in the fin 72. Intensity of the electromagnetic waves is adjusted to intensity that enables the magnetic material to generate a heat quantity appropriate for bonding of the strip portion 79 to the base tube 71.

Further, the second resin is coagulated by cooling the melted second resin in the strip portion 79 (a step S108). At this time, if the first resin has been fused in the portion of the base tube 71 abutting on the strip portion 79, the melted first resin is likewise coagulated. When the fused second resin is coagulated, the strip portion 79 of the fin 72 is bonded to the outer peripheral surface of the base tube 71 (a step S109).

It is to be noted that, the distal side inclined surface 81 and the proximal side inclined surface 82 are bonded to the outer peripheral surface of the base tube 71 through an adhesive or the like. When the distal side inclined surface 81 is bonded, a protrusion amount of the fin 72 toward the outer peripheral direction is reduced as getting toward the distal direction on the distal direction side with respect to the distal side reference position Q1 Further, when the proximal side inclined surface 82 is bonded, the protrusion amount of the fin portion 72 is reduced in the radial direction (the outer peripheral direction) of the base tube 71 as getting toward the proximal direction on the proximal direction side with respect to the proximal side reference position Q2.

As described above, in the spiral unit 30, when the electromagnetic waves are applied, the magnetic material is vibrated, and the second resin is fused in the strip portion 79, thereby bonding the strip portion 79 of the fin 72 to the outer peripheral surface of the base tube 71. Since an adhesive or the like that is hardened by ultraviolet rays is not used, bonding of the strip portion 79 to the outer peripheral surface of the base tube 71 is not affected by a shelf time of the adhesive or a dispensing issue. Furthermore, since a solvent is not used, it does not require a long time to bond the fin 72 to the base tube 71, and hence safety of a manufacturer can be assured.

Moreover, in the spiral unit 30, when the fin 72 is wound on the outer peripheral surface of the base tube 71 in a state where the strip portion 79 abuts on the outer peripheral surface of the base tube 71, the strip portion 79 can be easily bonded to the outer peripheral surface of the base tube 71. Thus, in the fin 72, providing the strip portion 79 in a position where it can abut on the outer peripheral surface of the base tube 71 can suffice and, for example, a surface of the fin 72 (the strip portion 79) which is to be bonded to the base tube 71 does not have to be formed into a planar shape. Thus, the shape of the fin 72 is not restricted as long as the strip portion 79 can abut on the outer peripheral surface of the base tube 71.

Additionally, since the second resin of the strip portion 79 is fused due to the heat generated by the vibration of the magnetic material, a filler member or the like does not have to be provided in the bonding portions of the fin 72 and the base tube 71. Further, the fin 72 including the strip portion 79 containing the magnetic material is easily formed by two-color extrusion molding. Thus, in manufacture of the spiral unit 30, a time is shortened, and costs can be decreased.

As described above, in the spiral unit 30 according to this embodiment, the fin 72 having any shape can be easily and safely bonded to the outer peripheral surface of the base tube 71. Consequently, the spiral unit 30 can be readily manufactured.

Furthermore, in the spiral unit 30, a strip width dimension L1 of the strip portion 79 in the fin width direction is smaller than a cavity width dimension L2 of the cavity portion 78 in the fin width direction. Thus, when the second resin is fused in the strip portion 79 by the vibration of the magnetic material, the cavity portion 78 is effectively prevented from communicating with the outside of the fin 72. Thus, when the second resin is fused in the strip portion 79, the tubular fin 72 including the hollow portion 77 can be effectively prevented from being deformed. That is, the shape of the fin 72 does not change in the cross section perpendicular to the fin axis F by the fusion of the second resin in the strip portion 79.

How to use the endoscope apparatus 1 which is the insertion apparatus adopting the spiral unit 30 will now be described. At the time of using the endoscope apparatus 1, in a state where the spiral unit 30 is attached to the inserting section 2, the inserting section 2 is inserted into, e.g., a lumen. Further, the motor 66 is driven in a state where the fin 72 abuts on a lumen paries, and the spiral unit 30 is rotated in one side of the periaxial direction of the longitudinal axis relative to the inserting section 2 as described above. When the spiral unit 30 (the base tube 71 and the fin 72) is rotated in one side of the periaxial direction of the longitudinal axis in a state where the fin 72 spirally extended around the longitudinal axis C receives pressing force from the lumen paries toward the inner peripheral direction, the propulsive force in the distal direction acts on the inserting section 2. Furthermore, in a state where the fin 72 receives the pressing force from the lumen paries in the inner peripheral direction, when the spiral 30 (the base tube 71 and the fin 72) is rotated in the other side of the periaxial direction of the longitudinal axis, the propulsive force in the proximal direction acts on the inserting section 2. Insertability of the inserting section 2 in the lumen are improved by the propulsive force in the distal direction, and removability of the inserting section 2 in the lumen can be improved by the propulsive force in the proximal direction.

Here, the fin 72 is formed into the tubular shape including the hollow portion 77, and hence the fin 72 has appropriately elasticity. Since the fin 72 has the appropriate elasticity, occurrence of torsion and twist in the fin 72 can be effectively avoided in a state where the pressing force acts on the fin 72 from the lumen paries toward the inner peripheral direction. Since the torsion and the twist do not occur in the fin 72, the propulsive force toward the distal direction or the proximal direction appropriately acts on the inserting section 2 by rotating the spiral unit 30. Thus, when the spiral unit 30 is rotated, the insertion and the removal of the inserting section 2 in the lumen can be appropriately performed.

Moreover, since the fin 72 is formed into the tubular shape including the hollow portion 77, the fin 72 has appropriate flexibility. Thus, even in a state where the spiral unit 30 is not rotated, the fin 72 can be easily bent by the pressing force from the lumen paries when moving the inserting section 2 toward the proximal direction in the lumen. Therefore, even if the spiral unit 30 fails to rotate due to a failure or the like, the inserting section 2 can be easily removed from the lumen.

(Modifications)

Figure 11:
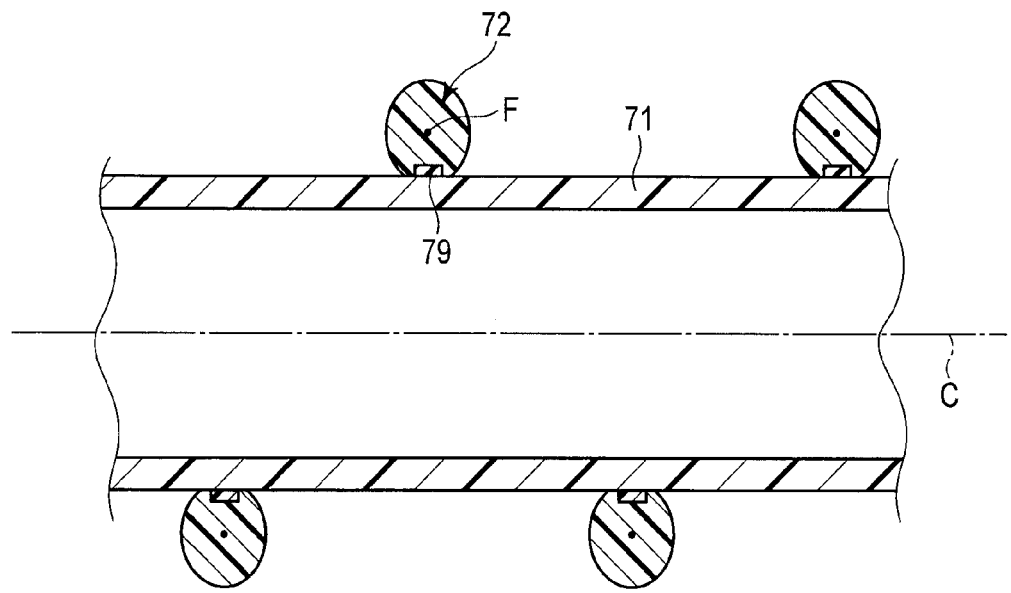
FIG. 11 is a cross-sectional view schematically showing the base tube and the fin in the cross section parallel to the longitudinal axis in the spiral unit according to a first modification.

It is to be noted that the fin 72 is formed into the tubular shape including the hollow portion 77 in the first embodiment, but it is not restricted thereto. For example, as a first modification, the fin 72 may be formed into a columnar shape rather than hollow shape as shown in FIG. 11. In this modification, a strip portion 79 in which a second resin is mixed with a magnetic material is likewise provided to the fin 72. Additionally, like the first embodiment, the fin 72 has a fin axis F spirally extended around a longitudinal axis C, and the strip portion 79 is extended along the fin axis F. Further, the fin 72 is bonded to an outer peripheral surface of a base tube 71 in the strip portion 79. That is, the strip portion 79 is provided in a position where it is bonded to the outer peripheral surface of the base tube 71 in the fin 72.

Figure 12:
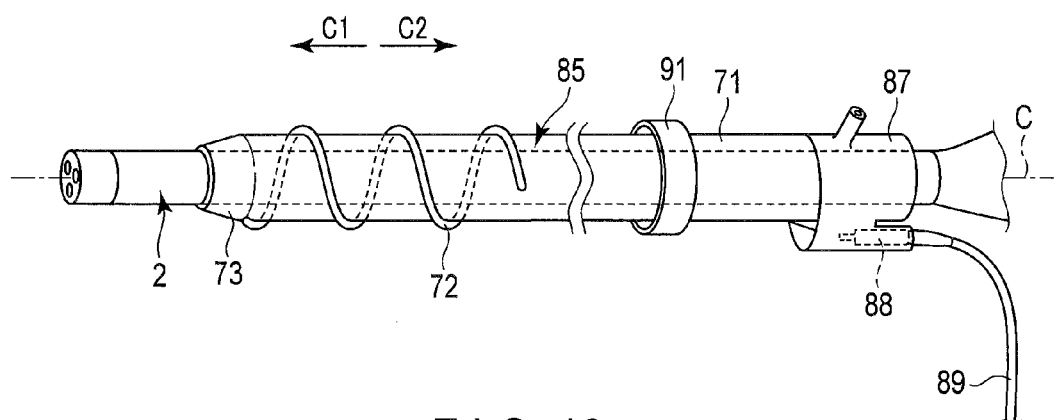
FIG. 12 is a perspective view schematically showing the spiral unit according to a second modification.

Further, although the motor 66 which is the drive member is attached to the member inserting section 65 of the operating section 3 in the first embodiment, it is not restricted thereto. For example, as a second modification, a motor 88 which is the drive member is provided to a spiral unit 85 shown in FIG. 12. The spiral unit 85 in this modification includes a proximal side tubular portion 87 in place of the proximal side taper portion 75. An inserting section 2 is inserted through the proximal side tubular portion 87, and the proximal side tubular portion 87 is fixed to the inserting section 2. Moreover, the motor 88 is attached to the proximal side tubular portion 87. Additionally, one end of a motor cable 89 is connected to the motor 88.

In this modification, a base tube 71 is coupled to a distal direction side of the proximal side tubular portion 87, and a fin 72 is disposed on an outer peripheral surface of a distal portion of the base tube 71. Further, a distal side taper portion 73 is provided on the distal direction side of the base tube 71. In this modification, the fin 72 is provided only on the outer peripheral surface of the distal portion of the base tube 71, and the fin 72 is provided on the outer peripheral surface of the base tube 71 over the non-entire length along a direction parallel to a longitudinal axis C. Furthermore, a tubular holding portion 91 is provided on an outer peripheral direction side of a proximal portion of the base tube 71.

In this modification, the base tube 71, the fin 72, and the distal side taper portion 73 can rotate in a periaxial direction of the longitudinal axis relative to the proximal side tubular portion 87. Thus, the base tube 71, the fin 72, and the distal side taper portion 73 can rotate in the periaxial direction of the longitudinal axis relative to the inserting section 2. Thus, in this modification, the non-entire of the spiral unit 85 can rotate in the periaxial direction of the longitudinal axis relative to the inserting section 2, but a part of the spiral unit 85 including the base tube 71 and the fin 72 can rotate in the periaxial direction of the longitudinal axis relative to the inserting section 2.

In this modification, rotational drive force that rotates the base tube 71 and the fin 72 is generated by supplying electric power to the motor 88 through the motor cable 89 to drive the motor 88. The generated rotational drive force is transmitted to the base tube 71 through a gear or the like (not shown) attached to the proximal side tubular portion 87, and the base tube 71, the fin 72, and the distal side taper portion 73 rotate in the periaxial direction of the longitudinal axis relative to the inserting section 2. Moreover, in this modification, like the first embodiment, a strip portion 79 in which a second resin is mixed with a magnetic material is provided in the fin 72.

Figure 13:
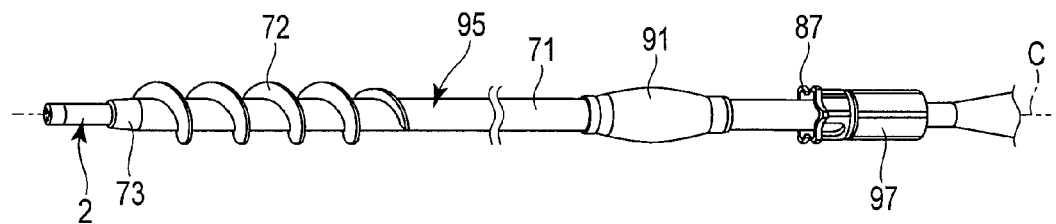
FIG. 13 is a perspective view schematically showing the spiral unit according to a third modification.

Additionally, in the first embodiment, the first modification, and the second modification, the rotational drive force that rotates the base tube 71 and the fin 72 in the periaxial direction of the longitudinal axis is generated by driving the motor (66; 88) with the supply of the electric power, but it is not restricted thereto. For example, as a third modification, a manual operation knob 97 may be provided in the spiral unit 95 in place of the motor (66; 88) as shown in FIG. 13. In this modification, like the spiral unit 85 according to the second modification, a base tube 71, a fin 72, a distal side taper portion 73, a proximal side tubular portion 87, and a holding portion 91 are provided to the spiral unit 95.

However, in this modification, on the proximal direction side of the proximal side tubular portion 87, the manual operation knob 97 is provided. The manual operation knob 97 can rotate together with the base tube 71, the fin 72, and the distal side taper portion 73 in the periaxial direction of the longitudinal axis relative to the proximal side tubular portion 87. Thus, the manual operation knob 97 can rotate together with the base tube 71, the fin 72, and the distal side taper portion 73 in the periaxial direction of the longitudinal axis relative to the inserting section 2.

In this modification, when the manual operation knob 97 is manually rotated in one side of the periaxial direction of the longitudinal axis, the rotational drive force that rotates the base tube 71 and the fin 72 is generated. The generated rotational drive force is transmitted to the base tube 71, and the base tube 71, the fin 72, and the distal side taper portion 73 rotate in the periaxial direction of the longitudinal axis relative to the inserting section 2. Further, in this modification, like the first embodiment, a strip portion 79 in which a second resin is mixed with a magnetic material is provided in the fin 72.

Furthermore, in the foregoing embodiment and modifications, although the endoscope apparatus 1 has been described as the insertion apparatus, the insertion apparatus is not restricted to the endoscope apparatus 1. For example, the spiral unit (30; 85; 95) may be attached to an inserting section of a manipulator apparatus which is the insertion apparatus.

That is, the spiral unit (30; 85; 95) may include the base tube extended along the longitudinal axis C and made of the first thermoplastic resin, and the fin 72 which is disposed on the outer peripheral surface of the base tube 71 along the fin axis F spirally extended around the longitudinal axis C and which is made of the second thermoplastic resin. Furthermore, the fin 72 could be provided in a state of being bonded to the outer peripheral surface of the base tube 71, and include the strip portion 79 spirally extended along the fin axis F. Moreover, in the strip portion 79, the second resin is to be mixed with the magnetic material.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A spiral unit comprising:
   a base tube which is extended along a longitudinal axis, and which is made of a first thermoplastic resin;
   a fin which is disposed on an outer peripheral surface of the base tube along a fin axis spirally extended around the longitudinal axis, and which is made of a second thermoplastic resin, the fin including a hollow portion in which a cavity portion is formed along the fin axis;
   a strip portion which is provided in a state of being bonded to the outer peripheral surface of the base tube in the fin, and which is spirally extended along the fin axis on an inner peripheral direction side of the cavity portion; and
   a magnetic material which is mixed with the second resin in the strip portion, and which is configured to generate heat when vibrated to fuse the second resin.

2. The spiral unit according to claim 1,
   wherein, in a cross section perpendicular to the fin axis, a strip width dimension of the strip portion in a fin width direction, which is a direction perpendicular to the fin axis and also perpendicular to a radial direction of the base tube, is smaller than a cavity width dimension of the cavity portion in the fin width direction.

3. An insertion apparatus comprising:
   the spiral unit according to claim 1; and
   an inserting section which is extended along the longitudinal axis, and to which the spiral unit is attached in a state of being inserted through the spiral unit.

4. The insertion apparatus according to claim 3,
   wherein, in a state where the spiral unit is attached to the inserting section, the base tube and the fin are integrally rotatable in a periaxial direction of the longitudinal axis relative to the inserting section.

5. A manufacturing method of a spiral unit, comprising:
   forming a base tube along a longitudinal axis from a first thermoplastic resin;
   forming a fin along a fin axis from a second thermoplastic resin, the fin being formed in a state where a strip portion in which the second resin is mixed with a magnetic material is extended along the fin axis;
   winding the fin on an outer peripheral surface of the base tube in a state where the fin axis is spirally extended around the longitudinal axis, the fin being wound in a state where the strip portion abuts on the outer peripheral surface of the base tube; and
   generating heat in the strip portion by applying electromagnetic waves to vibrate the magnetic material, the heat performing at least one of fusing the second resin in the strip portion and fusing the first resin in an abutting portion of the base tube to the strip portion, and thereby bonding the strip portion to the outer peripheral surface of the base tube.

6. The manufacturing method according to claim 5,
   wherein bonding the strip portion to the outer peripheral surface of the base tube includes cooling the fused first resin and/or the fused second resin to coagulate the first resin and/or the second resin.

* * * * *